United States Patent
Siegel et al.

(10) Patent No.: US 9,173,678 B2
(45) Date of Patent: *Nov. 3, 2015

(54) TRANSOBTURATOR LEAD IMPLANTATION FOR PELVIC FLOOR STIMULATION

(75) Inventors: Steven W. Siegel, North Oaks, MN (US); Eric H. Bonde, Minnetonka, MN (US); Martin T. Gerber, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 1536 days.

This patent is subject to a terminal disclaimer.

(21) Appl. No.: 12/819,780

(22) Filed: Jun. 21, 2010

(65) Prior Publication Data

US 2010/0262158 A1   Oct. 14, 2010

Related U.S. Application Data

(63) Continuation of application No. 11/338,611, filed on Jan. 24, 2006, now Pat. No. 7,763,034.

(51) Int. Cl.

| A61B 17/00 | (2006.01) |
|---|---|
| A61B 17/34 | (2006.01) |
| A61N 1/02 | (2006.01) |
| A61N 1/05 | (2006.01) |
| A61N 1/36 | (2006.01) |

(52) U.S. Cl.
CPC ............. *A61B 17/3468* (2013.01); *A61N 1/02* (2013.01); *A61N 1/0551* (2013.01); *A61B 17/3415* (2013.01); *A61B 17/3421* (2013.01); *A61B 2017/00039* (2013.01); *A61B 2017/00238* (2013.01); *A61B 2017/00805* (2013.01); *A61N 1/0558* (2013.01); *A61N 1/36007* (2013.01)

(58) Field of Classification Search
None
See application file for complete search history.

(56) References Cited

U.S. PATENT DOCUMENTS

| 4,141,365 A | 2/1979 | Fischell et al. |
|---|---|---|
| 4,512,351 A | 4/1985 | Pohndorf |

(Continued)

FOREIGN PATENT DOCUMENTS

| EP | 0278937 A2 | 8/1988 |
|---|---|---|
| EP | 1 048 270 A1 | 11/2000 |

(Continued)

OTHER PUBLICATIONS

Response to Examination Report dated Jul. 16, 2014, from counterpart European Patent Application No. 07762397.3, dated Nov. 10, 2014, 4 pp.

(Continued)

*Primary Examiner* — Kennedy Schaetzle
(74) *Attorney, Agent, or Firm* — Shumaker & Sieffert, P.A.

(57) ABSTRACT

The disclosure is directed to a method and tool for implanting a stimulation lead or other medical device adjacent a pudendal nerve. The tool includes a shaped needle that enters a patient and passes through an obturator foramen passage in a pelvis. A physician places a tip of the tool at the pudendal nerve and performs test stimulation to confirm an effective stimulation location. A shape memory cannula initially covering the needle remains at the pudendal nerve when the physician removes the tool. The cannula deforms to follow the curve of the pudendal nerve once the needle is removed, and a lead is inserted into the cannula and secured at the pudendal nerve placement site. This method may provide an easier and more consistent procedure for implanting the stimulation lead near the pudendal nerve.

17 Claims, 13 Drawing Sheets

(56) References Cited

U.S. PATENT DOCUMENTS

| | | | |
|---|---|---|---|
| 4,808,157 | A | 2/1989 | Coombs |
| 5,255,691 | A | 10/1993 | Otten |
| 5,443,492 | A | 8/1995 | Stokes et al. |
| 5,562,695 | A | 10/1996 | Obenchain |
| 5,669,882 | A | 9/1997 | Pyles |
| 5,899,909 | A | 5/1999 | Claren et al. |
| 6,104,957 | A | 8/2000 | Alo et al. |
| 6,249,707 | B1 | 6/2001 | Kohnen et al. |
| 6,360,750 | B1 | 3/2002 | Gerber et al. |
| 6,553,264 | B2 | 4/2003 | Redko et al. |
| 6,587,733 | B1 | 7/2003 | Cross, Jr. et al. |
| 6,735,474 | B1 * | 5/2004 | Loeb et al. ............ 607/41 |
| 6,847,849 | B2 | 1/2005 | Mamo et al. |
| 6,941,171 | B2 | 9/2005 | Mann et al. |
| 6,971,393 | B1 | 12/2005 | Mamo et al. |
| 6,978,180 | B2 | 12/2005 | Tadlock |
| 7,763,034 | B2 * | 7/2010 | Siegel et al. .......... 606/129 |
| 2002/0055761 | A1 * | 5/2002 | Mann et al. ............ 607/41 |
| 2002/0147485 | A1 | 10/2002 | Mamo et al. |
| 2003/0028147 | A1 | 2/2003 | Aves et al. |
| 2003/0045919 | A1 | 3/2003 | Swoyer et al. |
| 2003/0171644 | A1 | 9/2003 | Anderson et al. |
| 2003/0176875 | A1 | 9/2003 | Anderson et al. |
| 2003/0212305 | A1 | 11/2003 | Anderson et al. |
| 2004/0193228 | A1 | 9/2004 | Gerber |
| 2004/0210209 | A1 | 10/2004 | Yeung et al. |
| 2004/0210245 | A1 | 10/2004 | Erickson et al. |
| 2005/0010237 | A1 | 1/2005 | Niazi |
| 2005/0033372 | A1 | 2/2005 | Gerber |
| 2005/0055063 | A1 | 3/2005 | Loeb et al. |
| 2005/0070969 | A1 | 3/2005 | Gerber |
| 2005/0096667 | A1 | 5/2005 | Smith et al. |
| 2005/0159797 | A1 | 7/2005 | Chandran et al. |
| 2005/0240238 | A1 | 10/2005 | Mamo et al. |
| 2005/0267555 | A1 | 12/2005 | Marnfeldt et al. |
| 2006/0004421 | A1 * | 1/2006 | Bennett et al. ........ 607/41 |
| 2006/0015131 | A1 | 1/2006 | Kierce et al. |
| 2006/0058575 | A1 | 3/2006 | Zaddem et al. |
| 2006/0089633 | A1 | 4/2006 | Bleich et al. |
| 2006/0095079 | A1 | 5/2006 | Gerber |

FOREIGN PATENT DOCUMENTS

| | | |
|---|---|---|
| EP | 1 048 271 A2 | 11/2000 |
| EP | 1 342 454 A1 | 9/2003 |
| FR | 2 688 407 | 9/1993 |
| WO | WO 00/01320 | 1/2000 |
| WO | WO 00/33909 | 6/2000 |
| WO | WO 2005/032650 | 4/2005 |
| WO | WO 2005/105201 | 11/2005 |
| WO | WO 2005/118057 | 12/2005 |
| WO | 2007087190 A2 | 8/2007 |

OTHER PUBLICATIONS

Ishigooka et al., "A new technique for sacral nerve stimulation: a percutaneous method for urinary incontinence caused by spinal cord injury," British Journal of Urology, vol. 81, No. 2, pp. 315-318 (1998).

Abrams et al., "The role of neuromodulation in the management of urinary urge incontinence," British Journal of Urology, vol. 91, No. 4, pp. 355-359 (2003).

Spinelli et al., "New Percutaneous Technique of Sacral Nerve Stimulation Has High Initial Success Rate: Preliminary Results," European Urology, vol. 43, No. 1, pp. 70-74 (2003).

European Office Action dated Apr. 23, 2009 for corresponding EP Application No. 07 762 397.3-2305 (2 pgs.).

Notification of Transmittal of the International Preliminary Report on Patentability, dated Apr. 24, 2008 for corresponding PCT application No. PCT/US2007/001053 (13 pgs.).

Notification of Transmittal of the International Search Report and the Written Opinion, dated Jul. 18, 2007 for corresponding PCT application No. PCT/US2007/001053 (13 pgs.).

Office Action dated Jun. 4, 2010 for U.S. Appl. No. 11/739,982 (8 pgs.).

Responsive Amendment dated Sep. 7, 2010 for U.S. Appl. No. 11/739,982 (9 pgs.).

Office Action dated Oct. 22, 2010 for U.S. Appl. No. 11/739,982 (9 pgs.).

Response dated Dec. 20, 2010 for U.S. Appl. No. 11/739,982 (9 pgs.).

Examination Report from Counterpart European Patent Application No. 07762397.3, dated Jul. 16, 2014, 4 pp.

Response to Communication dated Apr. 23, 2009, from Counterpart European Patent Application No. 07762397.3, dated Nov. 2, 2009, 12 pp.

* cited by examiner

TRANSOBTURATOR LEAD IMPLANTATION FOR PELVIC FLOOR STIMULATION

This application is a continuation of U.S. patent application Ser. No. 11/338,611, which is entitled, "TRANSOBTURATOR LEAD IMPLANTATION FOR PELVIC FLOOR STIMULATION," and was filed Jan. 24, 2006. The entire content U.S. patent application Ser. No. 11/338,611, which published as U.S. Patent Application Publication No. 2007/0173900 on Jul. 26, 2007, is incorporated herein by reference in its entirety.

TECHNICAL FIELD

The disclosure relates to medical devices and, more particularly, surgical implantation tools.

BACKGROUND

Urinary incontinence, sexual dysfunction, and other pelvic floor disorders are common problems afflicting people of all ages, genders, and races. Many of the disorders may be associated with aging, injury or illness. In some cases, pelvic floor disorders can be attributed to improper nerve function. For example, aging can often result in nerve disorders that prevent proper operation of the bladder, sphincter muscles, or sexual organs. Nerves, such as the sacral nerve, pudendal nerve, or branches of the pudendal nerve, running though the pelvic floor regulate urinary and sexual function. Urinary incontinence or sexual dysfunction can arise when there is breakdown in communication within the nervous system.

Electrical stimulation of nerves in the pelvic floor may provide an effective therapy for a variety of disorders. For example, a surgeon may implant an electrical stimulation lead adjacent to the sacral nerve, pudendal nerve, or branches of the pudendal nerve. An implantable neurostimulator may be provided to deliver electrical stimulation through the lead. The stimulation may induce urinary sphincter constriction or reduce bladder wall constriction to aid the patient in reducing unwanted urinary voiding. Also, the stimulation may be effective in restoring sexual function or alleviating pelvic floor pain. Stimulation leads are ordinarily implanted surgically or percutaneously.

SUMMARY

The disclosure is directed to a method and tool for implanting a stimulation lead or other implantable medical device adjacent a pelvic nerve, such as the pudendal nerve. The tool includes a shaped introducer, such as a needle, that enters a patient and passes through a passage in a pelvis, such as the obturator foramen. A physician places a tip of the tool at the target nerve site and performs test stimulation to confirm an effective stimulation location.

A cannula initially covering the introducer remains at the nerve site when the physician removes the introducer. The cannula may have a shape memory property that permits it to deform to follow the curve of the pudendal nerve once the introducer is removed. A lead or other implantable medical device is inserted into the cannula and secured at the pudendal nerve placement site. This transobturator placement method may provide an easier and more consistent procedure for implanting a stimulation lead or other medical device near the pudendal nerve or other pelvic nerves.

Electrical stimulation of the pudendal nerve may provide therapy for patients experiencing urinary incontinence, urinary retention, bowel disorders such as fecal incontinence, constipation, sexual dysfunction, or other pelvic floor disorders related to pelvic nerve function. Alternatively, therapeutic stimulation may be induced by delivery of drugs or other substances. The transobturator procedure described herein may also be directed to the implantation of electrical leads adjacent other pelvic floor nerves. For example, the nerve of the clitoris may be accessed and stimulated to treat sexual dysfunction. In addition, the transobturator procedure may be applied to female or male patients.

In one embodiment, the disclosure provides a method for placing an implantable medical device in a pelvis of a patient, the method comprising creating a path through an opening in the pelvis, wherein the opening in the pelvis is an obturator foramen, and placing the implantable medical device via the path so that the implantable medical device is disposed adjacent to a nerve.

In another embodiment, the disclosure provides a system for placing an implantable medical device in a pelvis of a patient, the system comprising a handle, a needle, coupled to the handle, for insertion through an obturator foramen of the pelvis, and a cannula of a first shape having an inner lumen that receives at least a portion of the needle, wherein the needle is curved to facilitate insertion through the obturator foramen to extend to a nerve within the pelvis.

In an additional embodiment, the disclosure provides a method for placing an implantable lead for an electrical neurostimulator in a pelvis of a patient. The method comprises creating a path through an opening in the pelvis with a needle, wherein the opening in the pelvis is an obturator foramen, placing a cannula over the needle, introducing the cannula into the path, withdrawing the needle from the cannula, and inserting the implantable lead into the cannula so that the implantable medical device is disposed adjacent to a nerve.

In various embodiments, the disclosure may provide one or more advantages. For example, the transobturator implantation procedure may provide an easier and more consistent procedure for implanting the stimulation lead near the pudendal nerve. For example, the transobturator approach presents a number of anatomical landmarks, such as bone, muscle and ligament structures, that may be helpful in guiding an implantation tool to the desired nerve site. The transobturator implantation procedure may also reduce the risk of nerve tissue damage associated with other lead implantation procedures. In addition, an improved implantation procedure may not only decrease the time and cost associated with lead implantation, but increase the number of patients who may utilize pudendal nerve or other pelvic floor nerve stimulation to treat a variety of conditions. Further, transobturator implantation may utilize established skills of the physician. Additional advantages may include more secure placement of a lead, and resistance to movement of the lead due to placement through the obturator membrane. Also, there may be less chance of movement during activity such as intercourse with pudendal or clitoral nerve stimulation following lead implantation via the transobturator route. In some cases, external imaging techniques such as fluoroscopy may be unnecessary to achieve proper lead placement.

The details of one or more embodiments of the disclosure are set forth in the accompanying drawings and the description below. Other features, objects, and advantages of the disclosure will be apparent from the description and drawings, and from the claims.

DETAILED DESCRIPTION

Figure 1:
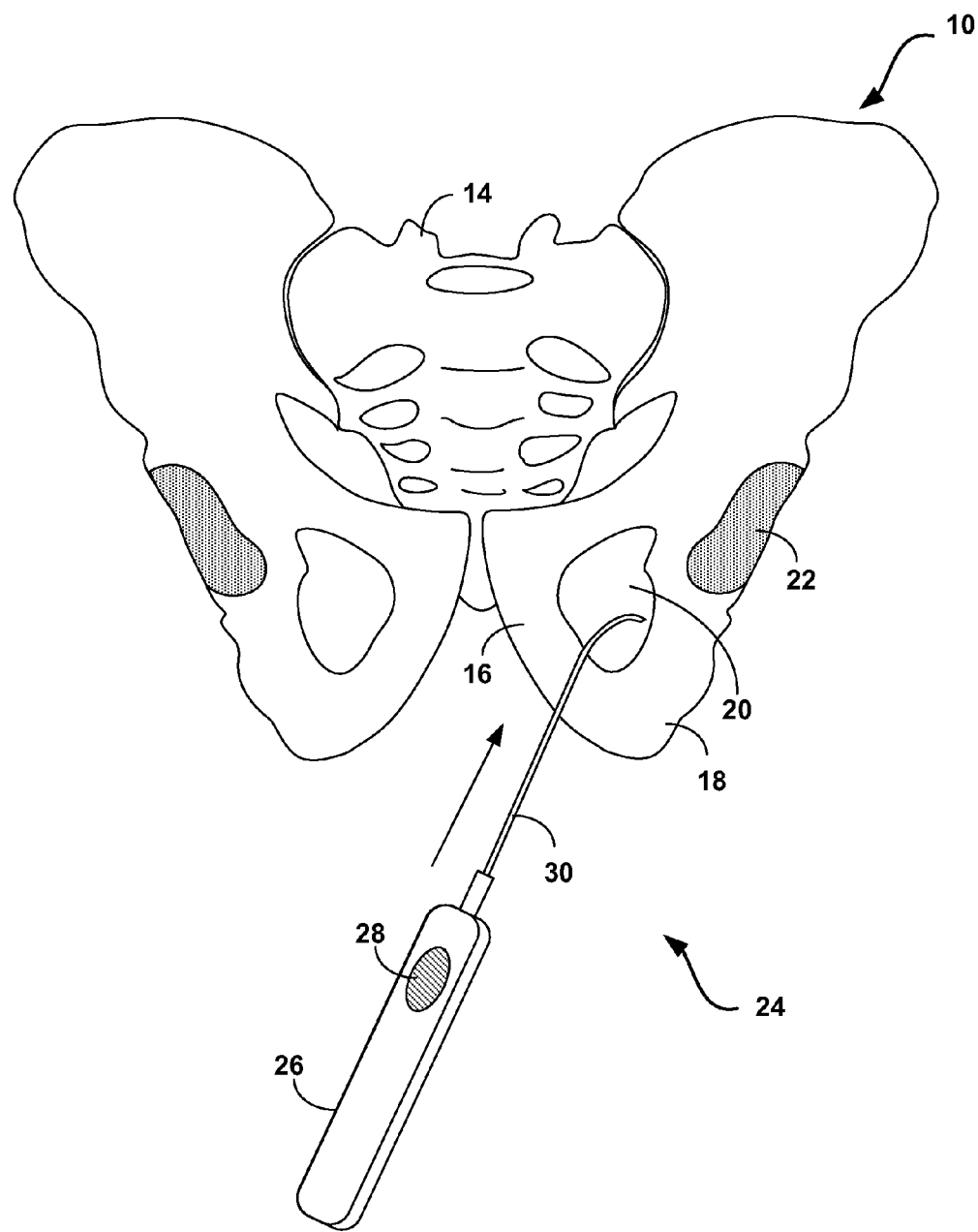
FIG. 1 is a schematic diagram illustrating an exemplary implant tool and method of inserting the tool through an obturator foramen of the pelvis for implantation of a medical device such as an electrical stimulation lead.

FIG. 1 is a schematic diagram illustrating an exemplary implant tool 24 and a method of inserting the tool through an obturator foramen of pelvis 10. As shown in FIG. 1, an anterior view of pelvis 10 includes sacrum 14, inferior pubic ramus 16, ischial tuberosity 18, obturator foramen 20 and acetabulum 22. Implant tool 24 includes housing 26, thumb rest 28 and needle 30. Implant tool 24 is used by a surgeon to locate a nerve in pelvis 10 for the purpose of implanting an electrical lead or other medical device that stimulates the nerve. An introducer, in the form of needle 30 in the example of FIG. 1, is inserted through obturator foramen 20 to access pelvic floor nerves of a patient. In this manner, needle 30 supports transobturator access to the pelvic floor nerves. Pelvic nerves may include sacral nerves, pudendal nerves, or branches of pudendal nerves, and other pelvic nerves.

Implant tool 24 may be used to reach a wide variety of nerves which can be accessed by the transobturator surgical procedure described herein. Some of these nerves include the pudendal nerve, various branches of the pudendal nerve, and the nerve of the clitoris, as well as other pelvic nerves. A transobturator method and implant tool 24 to implant an electrical stimulation lead adjacent to the pudendal nerve will be described herein as an example. Implant tool 24 may also be used to implant a lead at other nerves within pelvis 10. In some cases, the shape of implant tool 24 may be modified to facilitate lead placement proximate a target nerve or nerves.

Upon implantation of a distal end of the lead, a proximal end of the lead may be tunneled for connection to an implanted electrical neurostimulator or a lead extension coupled to the neurostimulator. In some embodiments, a catheter may be tunneled to deliver drugs to a nerve from an implantable or external drug infusion pump. In other embodiments, implant tool 24 may implant a leadless stimulator module so that a lead is not needed to be tunneled through patient 12. Needle 30, or any other needle described herein, may be any object that is introduced into or otherwise penetrates tissue of patient 12.

The pudendal nerve originates from sacrum 14 and runs along the pelvic floor before branching into other nerves that innervate organs and lower extremities. Minimally invasive methods for implanting an electrical lead adjacent the pudendal nerve are preferred, but involve risk in causing damage to surrounding healthy tissue, organs, or nerves. In addition, the use of imaging equipment to implant the lead may be cumbersome or impractical in some cases. Advantageously, using the transobturator method described in this disclosure, a physician ordinarily will be able to palpate anatomical landmarks, such as bone, muscle and ligament structures, to accurately locate the pudendal nerve. In this manner, implant tool 24 allows the physician to successfully locate the pudendal nerve and effectively position a lead adjacent the nerve.

A transobturator procedure using implant tool 24 is preferably performed on a patient having normal anatomical soft tissue covering pelvis 10 such as muscle, blood vessels, organs, and skin. FIG. 1 is for illustrative purposes and shows pelvis 10 without soft tissue surrounding pelvis 10. The patient lies in a modified lithotomy position to enable the physician to perform the procedure. The lithotomy position is a position in which a patient is on her or his back with the hips and knees flexed and the thighs apart. This position is often used with female patients for vaginal examinations and childbirth. Local or general anesthetics may be administered to minimize pain perceived by the patient. The physician locates obturator foramen 20 by palpating inferior pubic ramus 16 and ischial tuberosity 18 from inside of the vagina (not shown) for female patients, or from the inside of the rectum, e.g., for female or male patients. With a finger locating obturator foramen 20 from inside pelvis 10, the physician is able to identify bone landmarks that indicate a path for insertion of needle 30.

Using the example of a female patient, needle 30 pierces skin in the pubic area between the vagina and an adjacent leg. The leg is attached to acetabulum 22, so the leg limits entry angles of needle 30. Once underneath the skin, the physician follows the curve of needle 30 and advances implant tool 24 in the direction of the arrow through obturator foramen 20 to the approximate location of the pudendal nerve. In the case of different nerves, i.e., other than the pudendal nerve, a different curve of needle 30 may aid in directing needle 30 to the appropriate nerve site.

The final placement of needle 30 may be partially determined by the ischial spine (not shown), which is dorsal of the pudendal nerve. Ligaments near the pudendal nerve may also aid in guiding needle 30 to the correct placement position adjacent to the pudendal nerve. The sacrotuberous ligament provides a posterior stopping point for needle 30, while the sacrospinous ligament creates an anterior border around the pudendal nerve. The physician may use these ligaments to position the tip of needle 30 adjacent to the location of the pudendal nerve.

Handle 26 is shaped to allow a physician to hold it with one hand. Thumb rest 28 is also provided to the physician to support the simple hand motion of the transobturator procedure. Thumb rest 28 may be constructed of a soft rubber or plastic so that the physician's thumb does not slip during the procedure. Other ergonomic features of handle 26 may be provided as well. For example, the sides of handle 26 may follow the contours of a hand or fingers. In addition, soft or rubber pads may be placed where handle 26 contacts with the hand to provide a secure griping surface.

Implant tool 24 does not contain a lead when inserted into pelvis 10. Implant tool 24 does include a cannula (not shown) temporarily mounted on needle 30. The cannula is a hollow cylinder covering needle 30 and is of sufficient length to reach the pudendal nerve while a portion of the cannula remains outside of the patient. Once needle 30 is appropriately positioned near the pudendal nerve, the needle is removed from the cannula so that the cannula remains positioned adjacent to the pudendal nerve. A stylet and a lead are then inserted into the cannula which serves as a lead introducer to guide the lead to the location adjacent the pudendal nerve.

Once the lead is in place, the stylet and cannula are removed and the lead is left in place to provide electrical stimulation to the pudendal nerve. The lead is secured in place with tines, or other anchoring structure, on the lead that are embedded within tissue of the pelvis. For example, tines may be disposed within an obturator muscle covering obturator foramen 20. Tines on the lead may also be attached to other surrounding tissue. In other embodiments, the cannula may reside within needle 30 before being deployed into pelvis 10.

After the lead is placed near the pudendal nerve, it is tunneled through the patient to a trial stimulator or chronic stimulator that provides electrical stimulation therapy to the pudendal nerve through the implanted lead. The lead may exit the patient's skin when attached to an external trial stimulator to evaluate stimulation therapy. In some embodiments, a perctuaneous lead extension couples the lead to the external trial stimulator. In this manner, the lead may be used with an implantable electrical neurostimulator if desired. The external trial stimulator may be located on the patient to avoid implantation in the case where electrical stimulation therapy is not effective. The lead may also be tunneled to a subcutaneous area where a chronic stimulator is implanted.

The location at which the chronic stimulator is implanted may vary according to the health, condition or anatomy of the patient. Examples of possible locations for a chronic stimulator may include the lower back, buttocks, abdomen, or thigh. In each case, electrical stimulation is delivered through the electrodes of the lead implanted adjacent to the pudendal nerve via the transobturator technique described in this disclosure. The stimulator is programmed to deliver electrical stimulation therapy appropriate for treatment of urinary incontinence, sexual dysfunction, pelvic pain or other pelvic floor disorders.

In some embodiments, implant tool 24 may be completely disposable to eliminate possible contamination between different patients. In other embodiments, one or more components of implant tool 24 may be reusable to reduce equipment costs. For example, handle 26 may be reusable as it does not come into contact with the patient. Handle 26 may be sterilizable in the event that biological tissues come into contact with the handle. Needle 30 may be detachable and disposable. Alternatively, needle 30 may be autoclaved or chemically sterilized for use in implanting a lead into a different patient.

Introduction of a needle and cannula have been described above. In alternative embodiments, however, a hollow needle may be used. In this case, it may be possible to eliminate use of a cannula. Instead, a stylet and lead may be introduced via an inner lumen of the needle that extends through the obturator foramen. Accordingly, the inner lumen of the hollow needle may be sized to accommodate the lead, and the stylet within the inner lumen of the lead. In this manner, it is not necessary to place the needle, place the cannula, withdraw the needle, and then place the stylet and lead. Instead, the stylet and lead may be introduced via the needle, reducing the number of steps necessary for implantation of the lead. In many embodiments, however, it will be desirable to use a needle and cannula.

Figure 2:
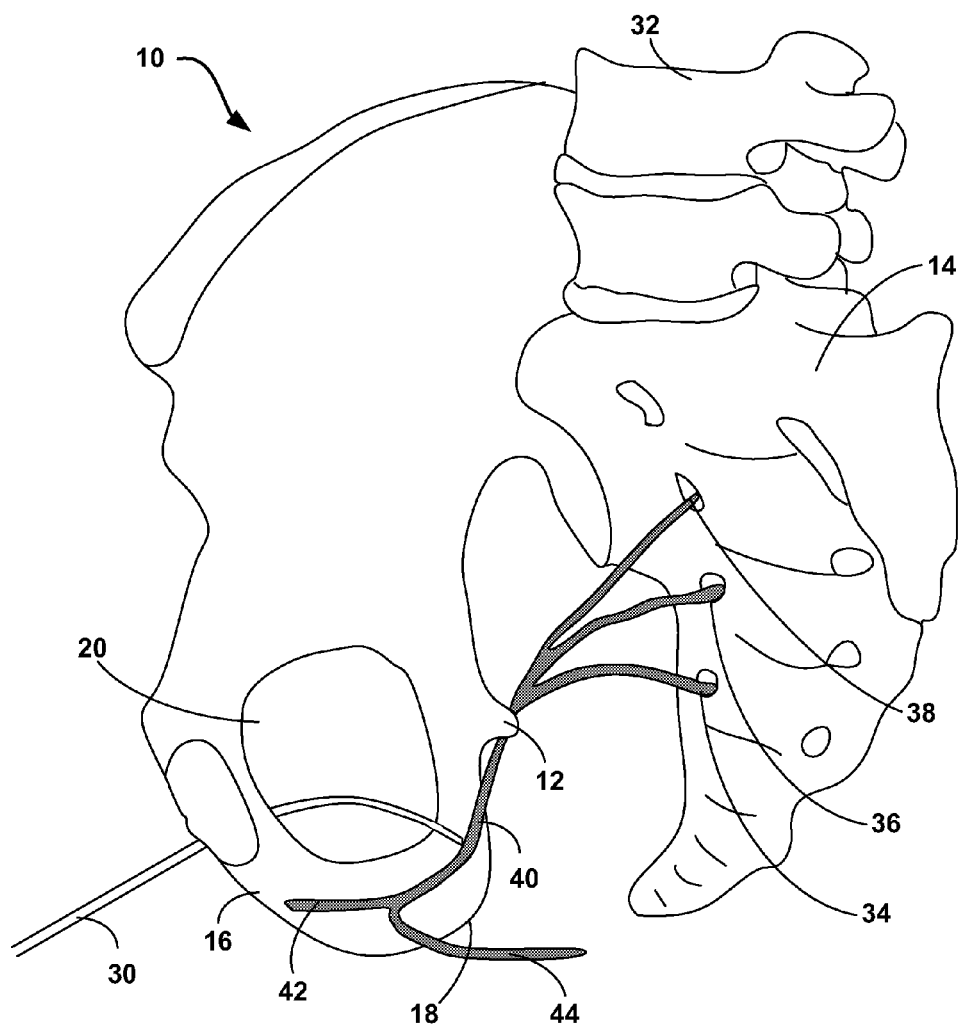
FIG. 2 is a schematic diagram illustrating the implant tool of FIG. 1 upon insertion through the obturator foramen to reach a pudendal nerve.

FIG. 2 is a schematic diagram illustrating an exemplary implant tool inserted through an obturator foramen to reach a pudendal nerve. In the example of FIG. 2, pelvis 10 includes sacrum 14, inferior pubic ramus 16, ischial tuberosity 18, obturator foramen 20, and ischial spine 12. FIG. 2 shows an interior view of pelvis 10. Vertebrae 32 are attached to sacrum 14 and protect the spinal cord (not shown) as it travels from the brain to pelvis 10. S2 nerve 34, S3 nerve 36, and S4 nerve 38 emanate from the spinal cord out from sacrum 14. Nerves 34, 36, and 38 combine posterior of ischial spine 12 to form pudendal nerve 40. Pudendal nerve 40 branches into perineal branch 42 and anal branch 44. Needle 30 is shown inserted through obturator foramen 20 into the interior of pelvis 10 and adjacent to pudendal nerve 40.

Pudendal nerve 40 may be difficult to access using surgical techniques as it is located deep within tissues of pelvis 10. Pudendal nerve 40 is surrounded by other nerves and important tissues, so accurate guidance of needle 30 may be difficult without internal guides when inserting needle 30. To aid in insertion, the physician may insert one or more fingers into a vagina or rectum of the patient (not shown) to palpate structures of pelvis 10. Through trans-vaginal or trans-rectal palpations, the physician may locate ischial tuberosity 18 as the inferior boundary of obturator foramen 20. The physician may also palpate ischial spine 12, which the physician may use to aim needle 30 through obturator foramen 20. The procedure may be performed trans-vaginally in a female patient, or in a male or female patient by palpating the bone landmarks through the rectum.

Inserting needle 30 into pelvis 10 with a transobturator procedure may be beneficial over other methods to reach pudendal nerve 40. Since there are no nerves passing over obturator foramen 20, it is unlikely that needle 30 would disturb another nerve near pudendal nerve 40. In addition, the physician needs only a simple hand motion to insert needle 30 adjacent to pudendal nerve 40. Anatomical structures may also aid in guiding needle 30 to the correct location. As mentioned previously, the sacrotuberous ligament (not shown) provides a posterior stopping point for needle 30 inferior to pudendal nerve 40. If the physician strikes the sacrotuberous ligament, needle 30 may be retracted slightly for good placement near pudendal nerve 40. The sacrospinous ligament (not shown) creates an anterior border around pudendal nerve 40. The physician may use these two ligaments to locate pudendal nerve 40 between the ligaments.

While the shape of needle 30 simplifies pudendal nerve isolation, other techniques may be useful in fine adjustment of the needle position. Instead of using strictly anatomical landmarks to position needle 30 adjacent pudendal nerve 40, imaging techniques such as fluoroscopy may be used in some embodiments. The physician also may rely on tactile feedback to guide placement, e.g., from needle 30 contacting ligaments, muscle bones or other structure. Alternatively, or additionally, implant tool 24 may be attached to or integrated with a test stimulator (not shown in FIG. 2) that produces electrical stimulation to verify accurate needle placement relative to the pudendal nerve. For example, as will be described in greater detail, the test stimulator may include an electrical stimulation pulse generator electrically coupled to needle 30 via an electrical conductor and electrically coupled to a ground electrode pad, which may be attached to an exterior location of the patient.

Needle 30 may include an electrode near the tip of the needle to deliver electrical pulses to pudendal nerve 40. Preferably, the majority of needle 30 is electrically insulated from the electrode so that stimulation energy can be generally confined to the needle tip. Hence, the electrode 30 may be provided by an electrically conductive needle 30, or a dedicated electrode (shown in FIGS. 4A and 4B) may be formed at or near a distal tip of needle 30, e.g., by deposition, crimping, welding, or other fabrication techniques. Upon delivery of stimulation energy to the electrode, the physician may identify muscle movement associated with appropriate pudendal nerve stimulation to correctly place needle 30. Alternatively, electromyography may be performed with the test stimulator or another device to observe a sphincter compound muscle action potential (CMAP) which aids in correct needle 30 placement. In either case, the test stimulator aids the physician in positioning needle 30 relative to the pudendal nerve.

A cannula (not shown in FIG. 2) may be located around needle 30, and utilized when implanting a lead. Needle 30 resides within an inner lumen defined by the cannula. The distal tip of needle 30 protrudes from a distal end of the cannula to provide a sharp needle point for penetration of tissue during the transobturator approach to the pudendal nerve 40. In other embodiments, needle 30 may comprise a dull or blunt point to limit tissue damage from contact with a sharp point. Once needle 30 is positioned correctly, the needle is removed from the cannula such that the cannula remains in place and the distal end of the cannula remains adjacent to pudendal nerve 40. The cannula provides an entry into the patient for implantation of the stimulation lead within pelvis 10. The cannula may be flexible and orient itself to follow pudendal nerve 40. The cannula may also be moved slightly without needle 30 for fine adjustment of the placement location. In some cases, the cannula may be slightly malleable so that the physician may customize the shape of the cannula to target a desired nerve site.

In other embodiments, needle 30 may be used to access other nerves in pelvis 10. For example, needle 30 may be inserted though obturator foramen 20 to reach the nerve of the clitoris located near inferior pubic ramus 16. Needle 30 may also be used to implant a lead or leadless electrical nerve stimulation module near perineal branch 42 or anal branch 44 of pudendal nerve 40. Needle 30 or the cannula may be shaped slightly differently to access nerves other than pudendal nerve 40.

Figure 3:
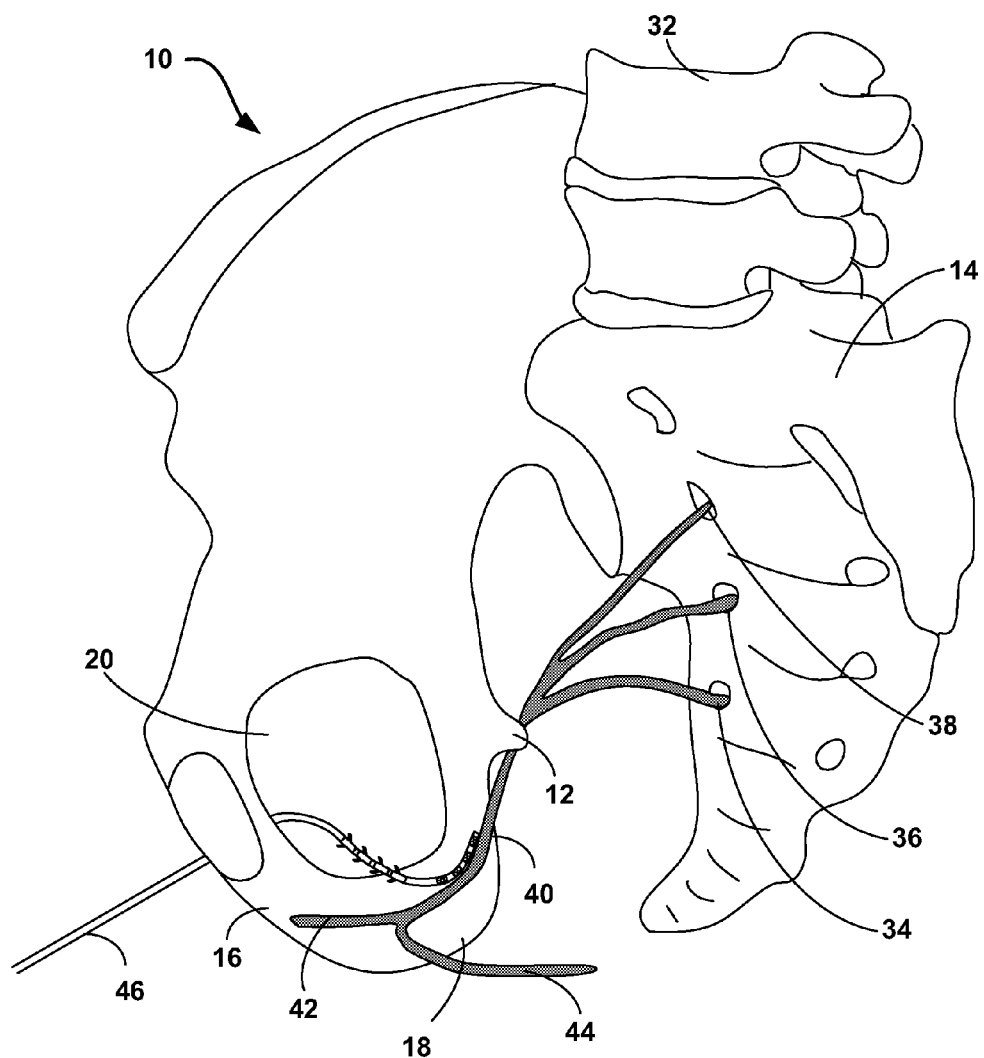
FIG. 3 is a schematic diagram illustrating an exemplary electrical lead implanted through the obturator foramen and disposed adjacent to a pudendal nerve.

FIG. 3 is a schematic diagram illustrating an exemplary electrical lead 46 implanted through an obturator foramen and disposed adjacent to a pudendal nerve. As shown in FIG. 3, lead 46 is implanted adjacent pudendal nerve 40 in pelvis 10. A stylet (not shown in FIG. 3) is used to guide lead 46 down the cannula (not shown in FIG. 3) and adjacent to pudendal nerve 40, e.g., for delivery of stimulation energy to alleviate urinary incontinence, fecal incontinence or sexual dysfunction. The cannula serves as a lead introducer. In some embodiments, test stimulation may be delivered from an external stimulator, or a test stimulator that is coupled to or integrated with tool 24, to ensure electrodes at the distal end of lead 46 are located in a correct position relative to pudendal nerve 40. If the location of lead 46 is incorrect, the cannula may be adjusted, either longitudinally or rotationally, to provide better electrical contact between the electrodes carried by lead 46 and pudendal nerve 40.

The cannula may be removed from lead 46 when the lead 46 provides good capture of pudendal lead 40. Lead 46 is disposed within a tunnel created by needle 30 and the cannula. Lead 46 may include tines or other structure to anchor the lead within tissue of pelvis 10. The transobturator procedure for lead implantation provides secure anchoring tissue for the tines of lead 46. For example, tines may be secured within the obturator muscle covering obturator foramen 20. Anchoring lead 46 within the obturator muscle may limit the amount of movement of lead 46 away from pudendal nerve 40. In some embodiments, other anchor mechanisms may be needed to secure lead 46 within patient 12. Some example anchor mechanisms may include screws, porous structures that allow tissue in-growth, or sutures.

Lead 46 is tunneled through tissue and coupled to a trial or chronic electrical stimulator (not shown in FIG. 3). In some embodiments, lead 46 may be coupled to a trial stimulator located external to the patient. A trial stimulator permits the physician and the patient to evaluate stimulation efficacy before implanting a stimulator. If stimulation therapy is unsuccessful, the trial stimulator is simply disconnected from lead 46 and the lead is removed from the patient. In other embodiments, lead 46 is tunneled subcutaneously to a location where a chronic stimulator is implanted beneath the skin. The chronic stimulator may provide months or years of stimulation therapy with the use of lead 46, so implantation of a chronic stimulator may be preferred. Lead 46 may be used by both a trial stimulator if therapy is successful, or lead 46 may be coupled to a chronic stimulator without using a trial stimulator for an evaluation period. In the case of trial stimulation, a percutaneous extension may be coupled to a chronically implanted lead to preserve sterile integrity of the chronically implanted lead.

An implanted chronic stimulator may be located at a variety of locations within the patient. Preferably, the implanted stimulator may be located near lead 46 and in a location that does not interfere with patient activity. For example, the stimulator may be located in the abdomen, buttocks, lower back, or thigh. In any location, lead 46 may be of sufficient length to reach both pudendal nerve 40 and the stimulator, either directly or via a lead extension coupled to the implanted stimulator.

In other embodiments, the distal end of lead 46 may be positioned adjacent other pelvic floor nerves. For example, lead 46 may be inserted into a cannula with a distal end positioned adjacent the nerve of the clitoris, e.g., for delivery of electrical neurostimulation to alleviate symptoms of sexual dysfunction or incontinence. In any nerve location, lead 46 may be implanted through obturator foramen 20. In some embodiments, however, lead 46 may not be tunneled through obturator foramen 20. In particular, lead 46 alternatively may be implanted through the obturator foramen 20 as described, but the proximal end of the lead may then be tunneled through another location of pelvis 10. In this case, the initial use of the transobturator approach ensures accurate lead placement relative to the pudendal nerve or other nerves, but the lead is then tunneled using a different path to reach the implanted stimulator. This lead 46 tunneling may be beneficial to reach certain stimulators or avoid a location of concern related to the health of the patient.

Figure 4A:
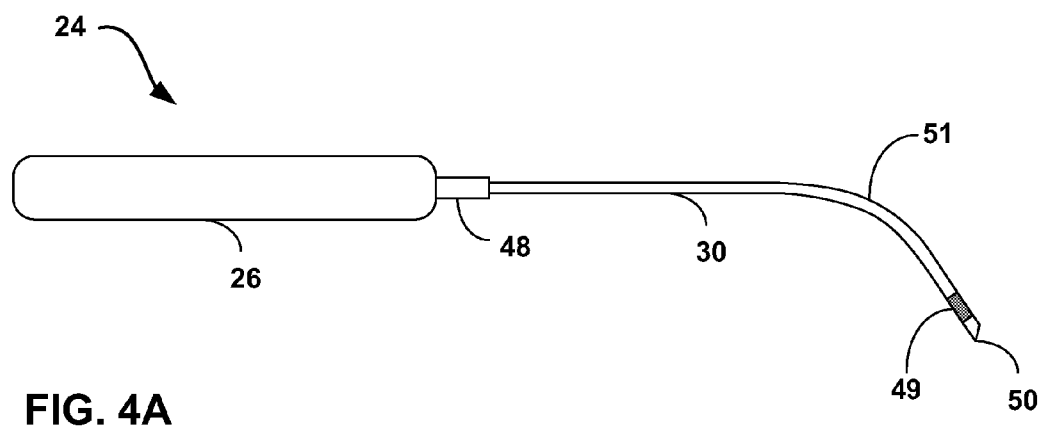
FIGS. 4A and 4B are views of an exemplary implant tool with a curved needle to implant an electrical stimulation lead adjacent to a pudendal nerve.
Figure 4B:
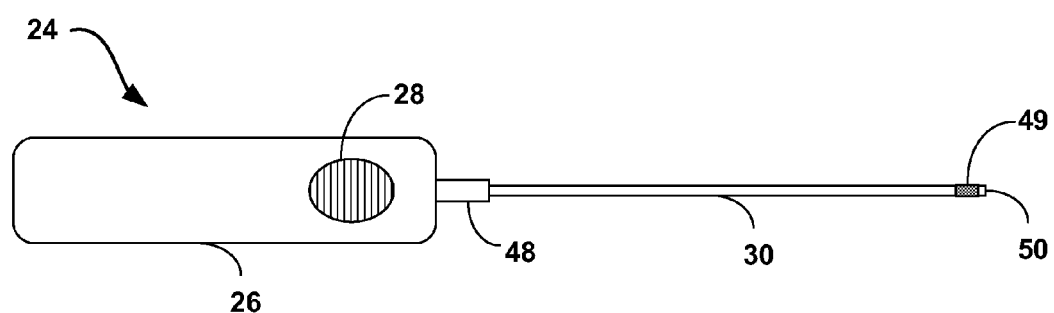

FIGS. 4A and 4B show views of exemplary implant tool 24 with a curved needle 30 to implant an electrical lead adjacent to a pudendal nerve. As shown in the side view of FIG. 4A, implant tool 24 includes handle 26, neck 48, needle 30, electrode 49 and tip 50. Handle 26 is generally rectangular in shape and has curved edges. Neck 48 securely attaches needle 30 to handle 26. Neck 48 may provide an attachment mechanism to enable needle 30 to be removed from neck 48. Detachment of needle 30 may be necessary if needle 30 is to be disposable or sterilizable separate from handle 26. Alternatively, neck 48 may be permanently attached to needle 30 and neck 48 is removable from handle 26.

Needle 30 is solid and curved at bend point 51 to facilitate entry through obturator foramen 20 and enable access to pudendal nerve 40. Tip 50 is used to pierce tissue and create a tunnel through pelvis 10. Tip 50 may be shaped similar to a wedge, cone, pyramid, or any other shape that includes decreased surface area at the distal end of needle 30 to define a sharp point. Needle 30 may be formed from a metal alloy such as stainless steel, aluminum or nitinol. An electrically conductive electrode 49 may be located near or on tip 50 for test stimulation during placement of needle 30. Electrode 49 may be cylindrical, circular, or rectangular in shape. Alternatively, the entire needle 30 may be electrically conductive. In this case, the majority of needle 30 may be covered with an electrically insulative coating or sleeve. Alternatively, a cannula placed over needle 30 may be electrically insulative.

Hence, the electrode may be formed at a distal end of needle 30 and coupled to an electrical conductor within the needle, or the entire needle may be electrically conductive, in which case an insulative coating, sleeve or cannula defines the size and length of the electrode at the distal end of needle 30. In each case, the insulative coating, sleeve or cannula limits stimulation energy to a small electrode area at the distal end of needle 30. In some other embodiments, an insulative coating, sleeve or cannula may define one or more window-like apertures that expose selected portions of the needle 30 to define one or more electrode regions either at the distal tip 50 or displaced some distance form the distal tip.

In some embodiments, needle 30 is hollow and open at tip 50. A hollow needle 30 may allow the inclusion of a visualization scope to enable the physician to view interior regions of pelvis 10 at tip 50 or permit the flow of a fluid to the tissue to lubricate or anesthetize the surrounding tissue or reduce tissue damage. In alternative embodiments, a hollow needle 30 may enable a lead to be inserted through the needle instead of through a cannula left within pelvis 10. Needle 30 may alternatively be capable of directly injecting a leadless electrical stimulation module that provides leadless electrical stimulation using a unitary, integrated stimulation module carrying one or more electrodes, stimulation pulse generation circuitry, and optionally telemetry circuitry.

Needle 30 may vary in length. Different sized patients may require different sizes of needle 30. In general, the length of needle 30 may be in a range of approximately 5 cm to 50 cm. More specifically, the length of needle 30 may be in a range of approximately 15 cm to 25 cm. In some cases, the length of needle 30 may be approximated by the height of the patient. In other cases, one length of needle 30 may be appropriate for any sized patient. Generally, the diameter of needle 30 may be in a range of approximately 1.0 mm to 5.0 mm. Needle may have a radius of curvature about bend point 51 in a range of approximately 2 cm to 20 cm, and more preferably approximately 5 cm to 15 cm, to permit ease of transobturator insertion to the desired nerve site.

In some embodiments, handle 26 may be formed in a cylindrical, spherical, or other ergonomic shape designed to be held by one hand. A generally cylindrical handle 26 shape may provide the most flexibility to a physician using implant tool 24. In other words, the physician may hold handle 26 at any circumference to direct needle 30 to any location. A cylindrical handle shape may also allow the physician to easily manipulate implant tool 24 when attempting to position needle 30 near pudendal nerve 40. For example, the physician may readily move handle 26 longitudinally and rotationally, as needed, during the transobturator process.

Handle 26 may generally be in a range of approximately 10 cm to 30 cm in length, 1 cm to 10 centimeter in width, and 0.5 cm to 5 cm in depth. Preferably, handle 26 may be in a range of approximately 10 cm to 15 cm in length, 2 cm to 4 cm in width, and 1 cm to 3 cm in depth. Handle 26 may be provided in different sizes to accommodate different sized hands of varying physicians. In addition, handle 26 may be made to accommodate use in a right or left hand, either as ambidextrous or separate models.

Handle 26 may be constructed of an injection moldable plastic such as polystyrene, polypropylene, polycarbonate, or any other polymer. In some embodiments, handle 26 may be constructed of a metal alloy including stainless steel or aluminum or a composite material. The material used to construct handle 26 may be dependent on the intended life of implant tool 24. For example, a disposable handle 26 may require an inexpensive plastic material, while a reusable handle 26 may require a more durable metal material. In addition to these materials, ergonomic rubber or similar material may be added to handle 26 to increase ease of use of implant tool 24.

Needle 30 may be constructed of a metal alloy with a strength and stiffness great enough to resist substantial bending upon insertion within pelvis 10. As mentioned above, such metals may include stainless steel, aluminum or nitinol. In some embodiments, a plastic material may be used to construct needle 30. If a plastic material is used, an electrical conductor may be provided within needle 30 for conduction of stimulation energy to an electrode formed at or adjacent to distal tip 50 of the needle. In some cases, needle 30 may be shaped by a physician.

FIG. 4B shows a top view of implant tool 24. Thumb rest 28 is provided on handle 26 to facilitate manipulation by a physician. Thumb rest 28 may be constructed of a soft rubber or other elastomeric material to provide comfort and friction between the thumb of a physician and handle 26. As shown in FIGS. 4A and 4B, needle 30 is curved in only one plane. In some embodiments, needle 30 may be curved outside of one plane to facilitate insertion of needle 30 into pelvis 10. For example, needle 30 may include a complex bend, such as a partial or full helical bend.

Figure 5A:
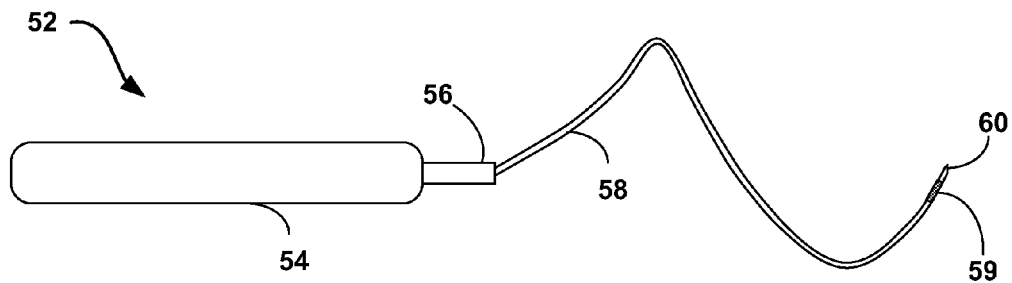
FIGS. 5A and 5B show views of an exemplary implant tool with a helical needle to implant an electrical lead adjacent to a pudendal nerve.
Figure 5B:
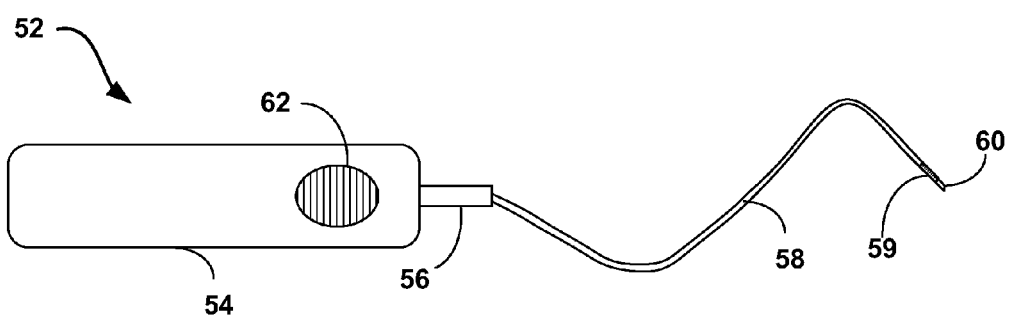

FIGS. 5A and 5B show views of exemplary implant tool 52 with needle 58 having a helical bend to implant an electrical lead adjacent to a pudendal nerve. As shown in FIG. 5A, implant tool 52 includes handle 54, neck 56, needle 58, electrode 59, and tip 60. Similar to handle 26, handle 54 is substantially rectangular in shape and has curved edges. Neck 56 securely attaches needle 58 to handle 54. In the example of FIGS. 5A and 5B, needle 58 is solid and curved to form a helical shape to facilitate entry through obturator foramen 20 and enable access to pudendal nerve 40.

Needle 58 is inserted into the patient and twisted about a long axis of handle 54 to pass through obturator foramen 20. The helix of needle 50 is shaped to facilitate accurate placement of needle 58 adjacent pudendal nerve 40. Tip 60 is used to pierce tissue and create a tunnel through pelvis 10. As in the example of FIGS. 4A and 4B, tip 60 may be shaped similar to a wedge, cone, pyramid, or any other shape that includes decreased surface area at the end of needle 58. An electrically conductive electrode 59 may be formed near or on tip 60, e.g., by any of the techniques described with respect to FIGS. 4A and 4B, for test stimulation during placement of needle 58. Electrode 59 may be cylindrical, circular, or rectangular in shape. Similar to implant tool 24, a cannula may also be used when implanting a lead. In some embodiments, needle 58 may be hollow and open at tip 60, e.g., to permit introduction of a visualization scope or a fluid into the interior of pelvis 10.

Helical needle 58 may vary in length, e.g., according to different size patients. In general, the length of needle 58 may be in a range of approximately 5 cm to 50 cm. More preferably, the length of needle 58 may be in a range of approximately 20 cm to 30 cm. The radius of the helix of needle 58 may be dependent on the individual patient. In general, the radius of curvature of needle 58 may be in a range of approximately 1 cm to 15 cm. More preferably, the radius of curvature of needle 58 may be in a range of approximately 2 cm to 10 cm. In addition, needle 58 may include more or less rotations of the helix. In the example of FIG. 5A, needle 58 includes a helix of approximately 360 degrees. Needle 58 may include as little as 90 degrees of a helix or as much as 720 degrees of a helix. Generally, the diameter of needle 58 may be in a range of approximately 1.0 mm to 5.0 mm.

In some embodiments, handle 54 may be cylindrical, spherical, or another ergonomic shape designed to be held by one hand. A cylindrical handle 54 shape may provide the most flexibility to a physician using implant tool 52. In other words, the physician may hold handle 52 at any circumference to direct needle 58 to any location. A cylindrical handle shape may also allow the physician to easily rotate and manipulate implant tool 52 when attempting to position needle 58 near pudendal nerve 40.

Similar to handle 26, handle 54 may generally be in a range of approximately 10 cm to 30 cm in length, 1 cm to 10 centimeter in width, and 0.5 cm to 5 cm in depth. Preferably, handle 26 may be in a range of approximately 10 cm to 15 cm in length, 2 cm to 4 cm in width, and 1 cm to 3 cm in depth. Handle 54 may be provided in different sizes to accommodate different sized hands of varying physicians.

Handle 54 may be constructed of materials similar to those described with reference to FIGS. 4A and 4B. Also, needle 58 may be constructed of a metal alloy with a strength and stiffness great enough to resist bending upon insertion within pelvis 10, as described with reference to needle 30. Such metals may include stainless steel, aluminum, or nitinol. In some embodiments, however, a plastic material may be used to construct needle 58, which may require an electrical conductor for delivery of stimulation energy to an electrode placed at or near distal tip 60.

FIG. 5B shows a top view of implant tool 52. Thumb rest 62 is provided on handle 54 to facilitate rotation and manipulation of implant tool 52 by a physician, and may be constructed as described with reference to FIGS. 4A and 4B. In operation, a physician penetrates obturator foramen with distal tip 60 of needle 58 and rotates handle 54 to move needle 30 into the interior of the pelvis such that distal tip 60 is placed adjacent a desired nerve site, such as the pudendal nerve.

Figure 6A:
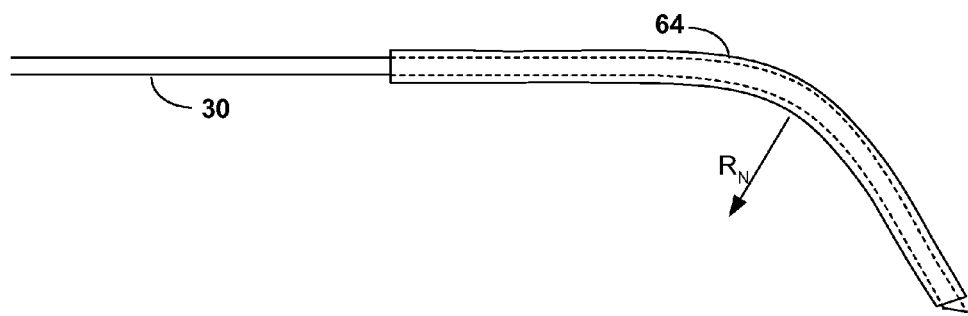
FIG. 6A shows the shape of an exemplary cannula on a needle of an implant tool.

FIG. 6A shows the shape of an exemplary cannula 64 mounted over needle 30 of an implant too 24. Needle 30 is within the inner lumen of cannula 64. Cannula 64 covers the outside of needle 30 before needle 30 is implanted within the patient. Cannula 64 is of sufficient length that the cannula may reach pudendal nerve 40 and completely exit the patient percutaneously, and is of sufficient diameter to allow a lead to slide within the inner lumen of cannula.

Cannula 64 may serve simply as a lead introducer, once needle 30 is removed from the patient. Alternatively, cannula 64 may perform the dual role of lead introducer and electrical insulator. As an electrical insulator, cannula 64 electrically insulates most of needle 30, but may be sized to permit a distal tip of the needle to be exposed. For embodiments in which needle 30 is electrically conductive, the distal tip of the needle may form an electrode region for delivery of stimulation energy on a test basis, while the remainder of the needle is insulated so that the stimulation energy is isolated to the electrode region.

Cannula 64 may be somewhat flexible to permit it to assume the shape of needle 30. As cannula 64 is placed over needle 30, for example, the cannula assumes a first shape, i.e., the shape of needle 30. The radius of curvature, $R_N$, of needle 30 may vary with regard to the patient. In general, as described previously, $R_N$ may be in a range of approximately 2 cm to 20 cm. More preferably, $R_N$ may be in a range of approximately 5 cm to 15 cm. In any case, the radius of curvature is used to reach pudendal nerve 40.

Cannula 64 is constructed of a flexible material with a shape memory in the material. The normal shape of cannula 64 may not be the shape of needle 30. In order for cannula 64 to aid in lead implantation, the cannula material may change shape once needle 30 is removed. Cannula 64 also may be electrically insulative. Cannula 64 may be constructed of a plastic capable of being thermoset, or heated to a certain shape. Such a polymer may include ethylene tetrafluoroethylene (ETFE). ETFE may also provide some torsional rigidity to aid in cannula 64 movement within pelvis 10. Other materials such as nitinol may be used to construct cannula 64 as well. Nitinol may provide an additional benefit in that it may be more readily visualized during fluoroscopy. Fluoroscopy may be used to aid in placement of needle 30 adjacent to pudendal nerve 40. In addition to the shape memory material of cannula 64, a coating may also be applied to the cannula. For example, a parylene or oxide film coating may be applied to cannula 64 in order to electrically insulate the cannula. Also, addition of a lubricating film or coating, such as PTFE, to the outer surface of cannula 64 may be desirable to facilitate insertion.

Figure 6B:
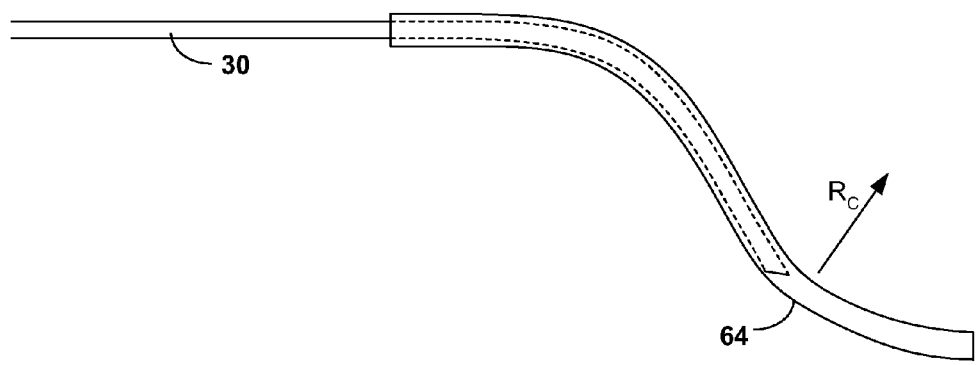
FIG. 6B shows the shape of an exemplary cannula as a needle of an implant tool is being removed from the cannula.

FIG. 6B shows the shape of exemplary cannula 64 as needle 30 of an implant tool is being removed from the cannula. As needle 30 is removed from cannula 64, the cannula changes conformation to a second shape. The second shape aids in guiding the distal tip of a lead along the side of pudendal nerve 40. The second shape is formed in the material of cannula 64, and assumes a radius of curvature $R_C$. $R_C$ may vary due to patient anatomy or nerve targeted to be stimulated. In general, $R_C$ is in a range of approximately 1 cm to 20 cm. More preferably, $R_C$ is in a range of approximately 2 cm to 10 cm.

As needle 30 is completely removed from cannula 64, the cannula remains in the second shape. A stylet and lead is then inserted into cannula 64. In particular, the stylet is inserted into an inner lumen defined by the lead, and the combined lead and stylet are then inserted into the inner lumen of cannula 64. Upon insertion into cannula 64, the lead is deflected to a location adjacent pudendal nerve 40, such as toward ischial spine 12. While cannula 64 is flexible, the physician may be able to slightly move cannula 64 while implanting the lead to the appropriate location. Once the lead is implanted, cannula 64 may be removed and disposed, leaving the stylet and lead in place within the pelvis of the patient. In some cases, cannula may be sterilized and reused in another procedure.

Figure 7A:
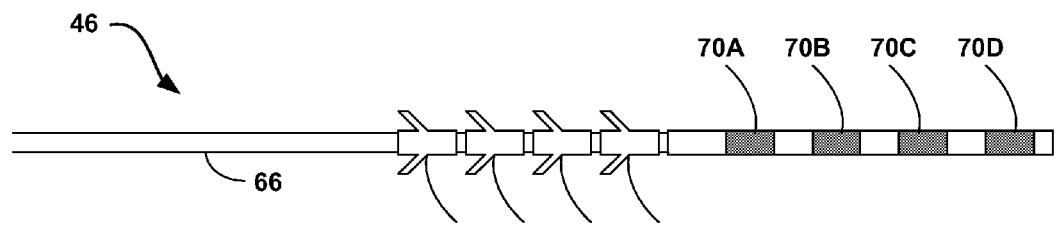
FIGS. 7A-7C show exemplary electrical leads with tines to secure the lead within a patient.
Figure 7B:
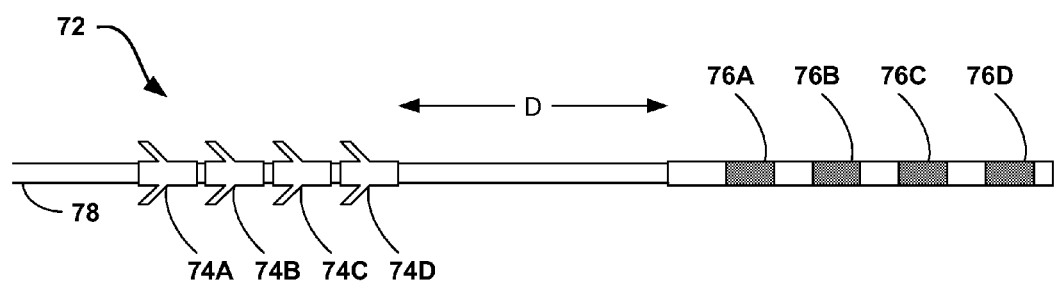
Figure 7C:
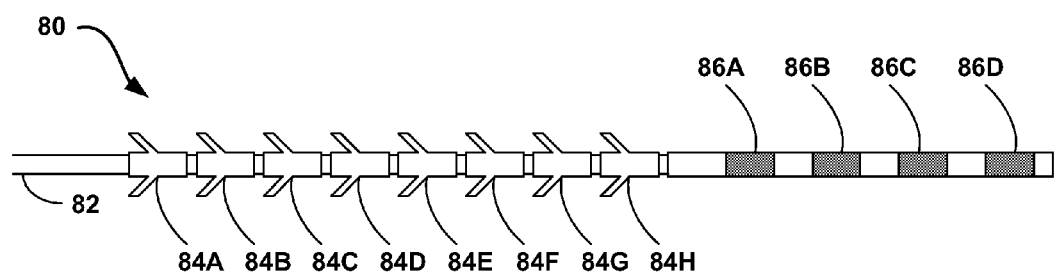

FIGS. 7A-7C show exemplary electrical leads with tines to secure the lead within a patient. As shown in FIG. 7A, lead 46 includes housing 66, tines 68A, 68B, 68C, and 68D (collectively tines 68), and electrodes 70A, 70B, 70C, and 70D (collectively electrodes 70). Lead 46 may be a standard lead that includes all four tines 68 close to electrodes 70. Implanting lead 46 may be beneficial due to tines 68 being anchored close to electrodes 70. A smaller distance between tines 68 and electrodes 70 may allow less movement of electrodes 70 with respect to adjacent pudendal nerve 40.

Electrodes 70 are more effective in delivering electrical stimulation when the electrodes are located close to pudendal nerve 40. If electrodes 70 migrate away from pudendal nerve 40, efficacy of stimulation therapy may decrease. Therefore, tines 68 located close to electrodes 70 may be beneficial to therapy efficacy. However, tines 68 may not be capable of anchoring into a solid tissue if they are located too close to electrodes 70. Since an obturator muscle may be some distance from pudendal nerve 40, tines 68 may only be able to anchor in less stable tissue.

FIG. 7B illustrates a lead 72 which includes housing 78, tines 74A, 74B, 74C, and 74D (collectively tines 74), and electrodes 76A, 76B, 76C, and 76D (collectively electrodes 76). Tines 74 are located a distance D away from the most proximal electrodes 76. Lead 72 may be capable of anchoring tines 74 in an obturator muscle while enabling electrodes 76 to reach further away from the anchoring point to pudendal nerve 40. Distance D may be generally in a range of approximately 0.5 cm to 10 cm, and more preferably 1 cm to 4 cm. While lead 72 may provide a more secure anchoring point, electrodes 76 may be free to migrate to an unacceptable distance away from pudendal nerve 40.

FIG. 7C illustrates a lead 80 which includes housing 82, tines 84A, 84B, 84C, 84D, 84E, 84F, 84G, and 84H (collectively tines 84), and electrodes 86A, 86B, 86C, and 86D (collectively electrodes 86). The increased number of tines 84 located on lead 80 may provide secure anchoring in an obturator muscle and soft tissue closer to pudendal nerve 40. Lead 80 may be capable of providing better anchoring points and eliminating migration of electrodes 86 with respect to pudendal nerve 40. However, removal of lead 80 may injure a greater volume of tissue. Therefore, lead 80 may be more appropriate for patients with more active lifestyles where lead migration may be a problem.

In any of leads 46, 72, and 80, any number of electrodes or tines may be implemented. Although leads 46, 72, 80 each include four electrodes, the leads may include one, two, four, eight or more electrodes. In addition, any number of tines may be used. Also, in some cases, it may be desirable to deploy two or more leads, each carrying one or more electrodes. Any of these configurations may be possible and desirable when implanting a lead to stimulation pudendal nerve 40 via the transobturator approach described in this disclosure. Other exemplary leads for urinary incontinence applications include the leads identified by model no. 3080, 3092, 3093, 3886, 3889 and 3966, and manufactured by Medtronic, Inc., of Minneapolis, Minn. Such leads and the leads described herein may be used in conjunction with the Model 3023 InterStim® implantable stimulator, also manufactured by Medtronic, Inc.

Figure 8:
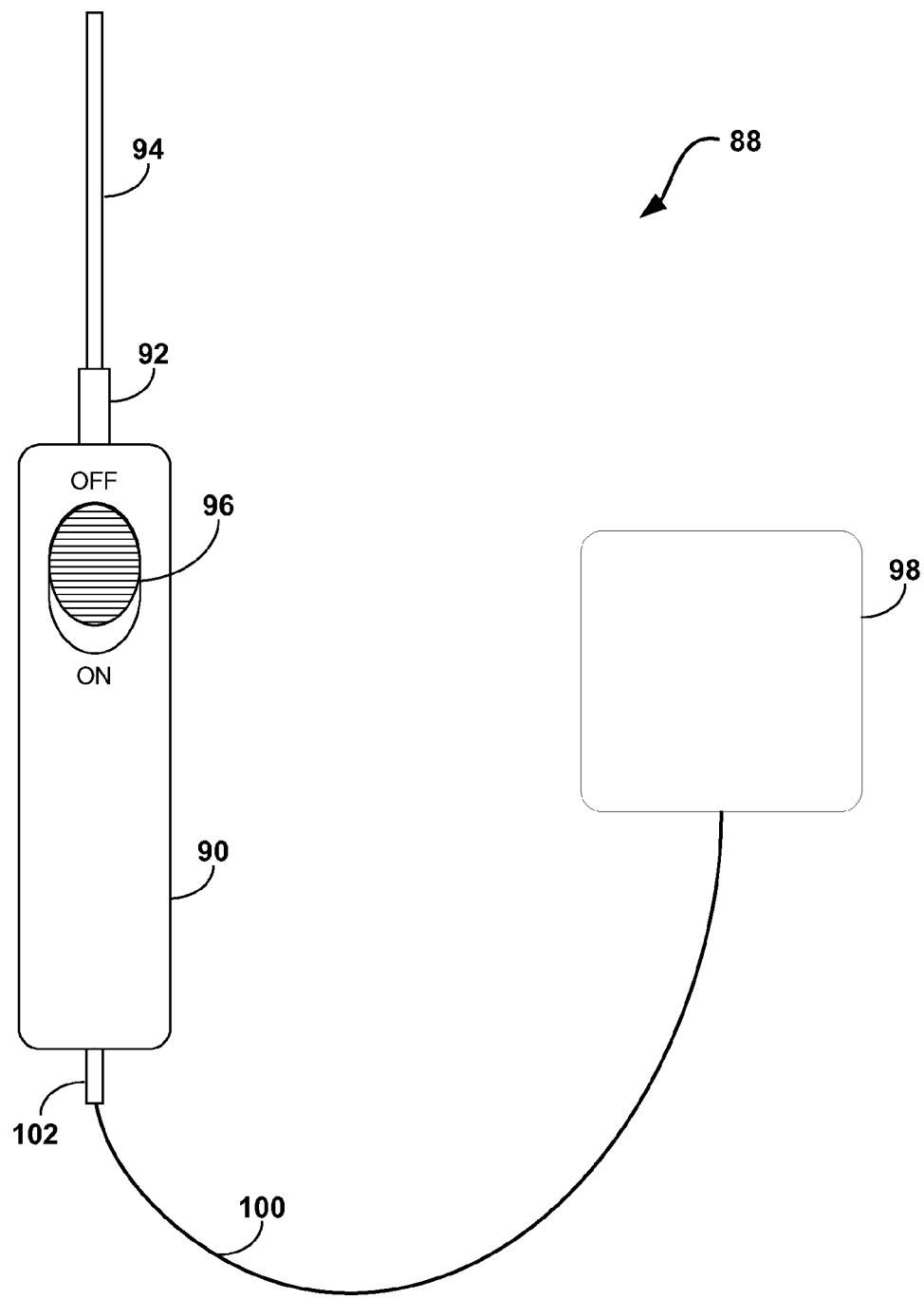
FIG. 8 is a schematic diagram illustrating an exemplary implant tool capable of providing test stimulation for determining correct lead placement.

FIG. 8 is a schematic diagram illustrating exemplary implant tool 88 capable of providing test stimulation for determining correct lead placement. As shown in FIG. 8, implant tool 88 is similar to implant tool 24 of FIG. 1. Implant tool 88 includes handle 90, neck 92, needle 94, switch 96, connector 102, cable 100, and ground electrode 98. Implant tool 88 may be used to implant a lead near pudendal nerve 40 using a transobturator approach, as described herein, and provide preliminary test stimulation without the need to implant a lead or couple needle 94 to an additional device. Handle 90 is also a housing which contains electronics and a power source necessary to provide test stimulation pulses when determining the correct placement of needle 94.

Needle 94 is curved similar to needle 30. Once needle 94 is correctly placed within pelvis 10, implant tool 88 may provide test stimulation pulses to specifically locate the best location to place a lead. The test stimulation pulses may be delivered via an electrode region at or near the distal tip of needle 94. Again, a dedicated electrode may be positioned at the distal tip, or the entire needle 94 may be electrically conductive but insulated to isolate stimulation to a region at or near the distal tip. Ground electrode 98 is placed on an external surface of the patient and forms another electrode so that unipolar stimulation can be delivered by the electrode carried by needle 94. An appropriate location for placement of ground electrode 98 may be the small of the back or the buttocks. Cable 100 is also connected to handle 90 with connector 102. The electrode at or near the distal end of the needle 94 delivers unipolar stimulation to the region of pudendal nerve 40. When the physician desires to analyze the location of the distal tip of needle 94 for proximity to the pudendal nerve 40, switch 96 is slid to the "ON" position to deliver test stimulation pulses. Switch 96 is moved to the "OFF" position once test stimulation is no longer needed.

Implant tool 88 may be programmed through a user interface located on the side of handle 90. Parameters such as voltage amplitude, current amplitude, pulse width, pulse frequency, duty cycle or other stimulation parameters may be adjusted before or during test stimulation. Alternatively, the parameters of the stimulation energy output from implant tool 88 may be fixed, or include a series of pulses with different parameters according to a predetermined sequence. In other embodiments, parameters may be adjusted by connecting a programmer to handle 90 through a wired connection or wireless telemetry.

As a further alternative, handle 90 may simply provide an electrical terminal for connection to an external test stimulator, and thereby serve as an electrical conduit between the test stimulator and needle 94. In addition, implant tool 88 may be able to store stimulation information and transfer the information to another device. In particular, implant tool 88 may include the capability to store stimulation information to memory to aid a physician in efficiently providing test stimulation.

In some embodiments, implant tool 88 may be capable of delivering bipolar test stimulation. Needle 94 may include more than one electrode to enable anode and cathode configurations for delivery of bipolar stimulation at or near the distal tip of the needle. In this case, ground electrode 98 would not be necessary. Bipolar stimulation may provide more accurate test stimulation of pudendal nerve 40, but may not readily allow for CMAP observation during placement of needle 94.

A cannula as described previously may be used with implant tool 88. Advantages of implant tool 88, in embodiments in which a stimulator is integrated with the tool, include fewer devices for the physician to operate and shorter implantation time of a lead to pudendal nerve 40. In other embodiments, implant tool 88 may include a channel though handle 90 and needle 94 to facilitate lead insertion directly though implant tool 88. Although needle 94 is shown as a simple needle, e.g., with a curve in one plane, needle 94 may be similar to helical needle 58.

Needle 94 may be disposable or sterilizable, similar to needle 30. Ground electrode 98 also may be disposable or sterilizable. Connector 102 and cable 100 may be disposable if permanently attached to a disposable ground electrode 98 or reusable if cable 100 temporarily attaches, such as with a clamp, to ground electrode 98.

Figure 9:
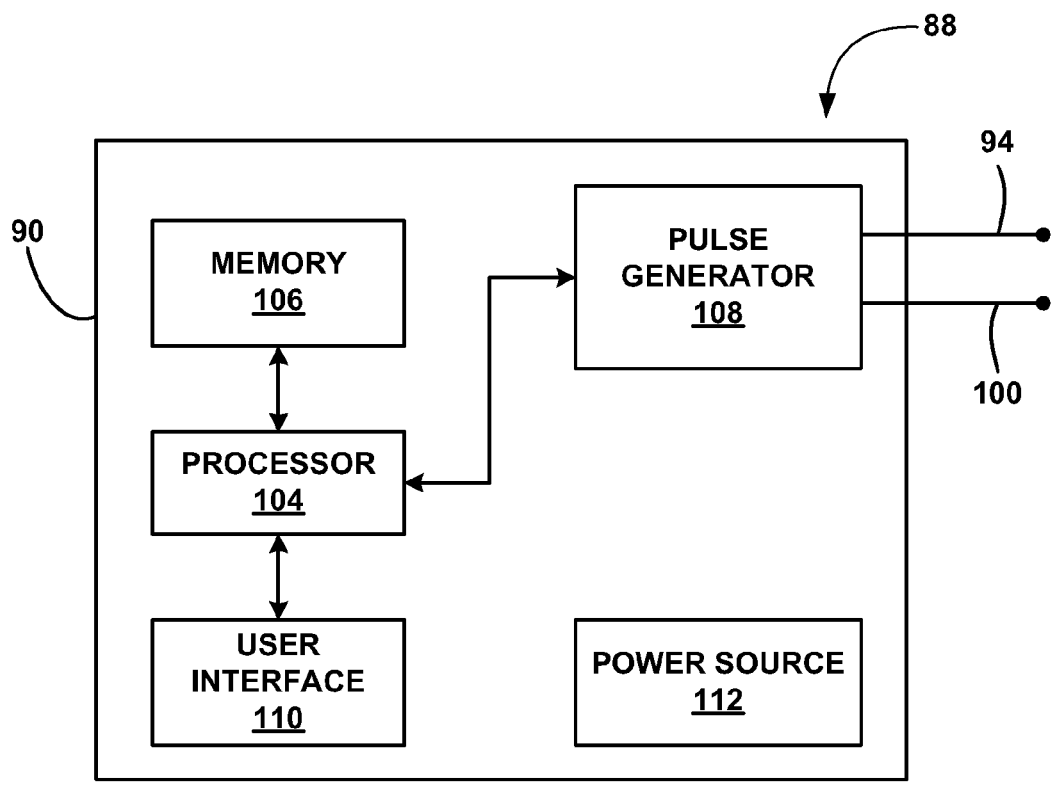
FIG. 9 is a functional block diagram illustrating various components of an implant tool capable of providing test stimulation.

FIG. 9 is a functional block diagram illustrating various components of implant tool 88 capable of providing test stimulation. Implant tool 88 includes handle 90, or housing 90. Components within housing 90 include processor 104, memory 106, pulse generator 108, user interface 110, and power source 112. Needle 94 includes at least one electrode and cable 100 is connected to ground pad 98. Memory 106 stores instructions for execution by processor 104, stimulation parameters and, optionally, information related to the use of needle 94. Memory 106 may include separate memories for storing instructions, stimulation parameter sets, and stimulation information, or a common memory.

Pulse generator 108 is programmed with stimulation pulse parameters appropriate for delivery of test stimulation in the form of stimulation pulses delivered continuously or in selected bursts. Pulse generator 108 may be substantially similar to a trial or chronic stimulator used to treat the patient. The physician may set test parameters for pulse generator 108 to reproduce.

Processor 104 controls pulse generator 108 to deliver electrical stimulation therapy. Based on stimulation parameters programmed by the physician through user interface 110, processor 104 instructs appropriate stimulation by pulse generator 108. Information may also be received from user interface 110 at any time during operation, in which case a change in stimulation parameters may immediately occur. User interface 100 may be accessed directly on handle 90 as a set of switches, dials, buttons, or other input media, or accessed via an external programmer that transmits information to tool 88 by wired or wireless telemetry. In some embodiments, wireless telemetry in implant tool 88 may be accomplished by radio frequency (RF) communication or proximal inductive interaction of implant tool 88 with another programming device via a telemetry interface (not shown). Processor 104 may control the telemetry interface to exchange information with the programming device. Processor 104 may transmit operational information and other information to the programming device via the telemetry interface.

Processor 104 determines any pulse parameter adjustments based on the received information, and loads the adjustments into memory 106 for use during delivery of stimulation. As mentioned above, user interface 110 may include a series of switches, dials, or buttons for changing stimulation parameters. User interface 110 also may include an LED or LCD display indicating the values of current stimulation parameters, battery life, and any operational information. Alternatively, user interface 110 may be a touch screen for modification of stimulation parameters. User interface 110 may be disabled by the physician during test stimulation to eliminate the chance of unsafe stimulation modifications during handling of handle 90.

Power source 112 delivers operating power to the components of implant tool 88. Power source 112 may include a battery and a power generation circuit to produce the operating power. In some embodiments, the battery may be rechargeable to allow extended operation Recharging may be accomplished through proximal inductive interaction between an external charger and an inductive charging coil within stimulator 12. In other embodiments, power source 112 may recharge though an alternating current adapter charger. Alternatively, power source 112 may directly utilize external power from an alternating current source, e.g., with appropriate isolation and ground fault interruption circuitry.

Figure 10:
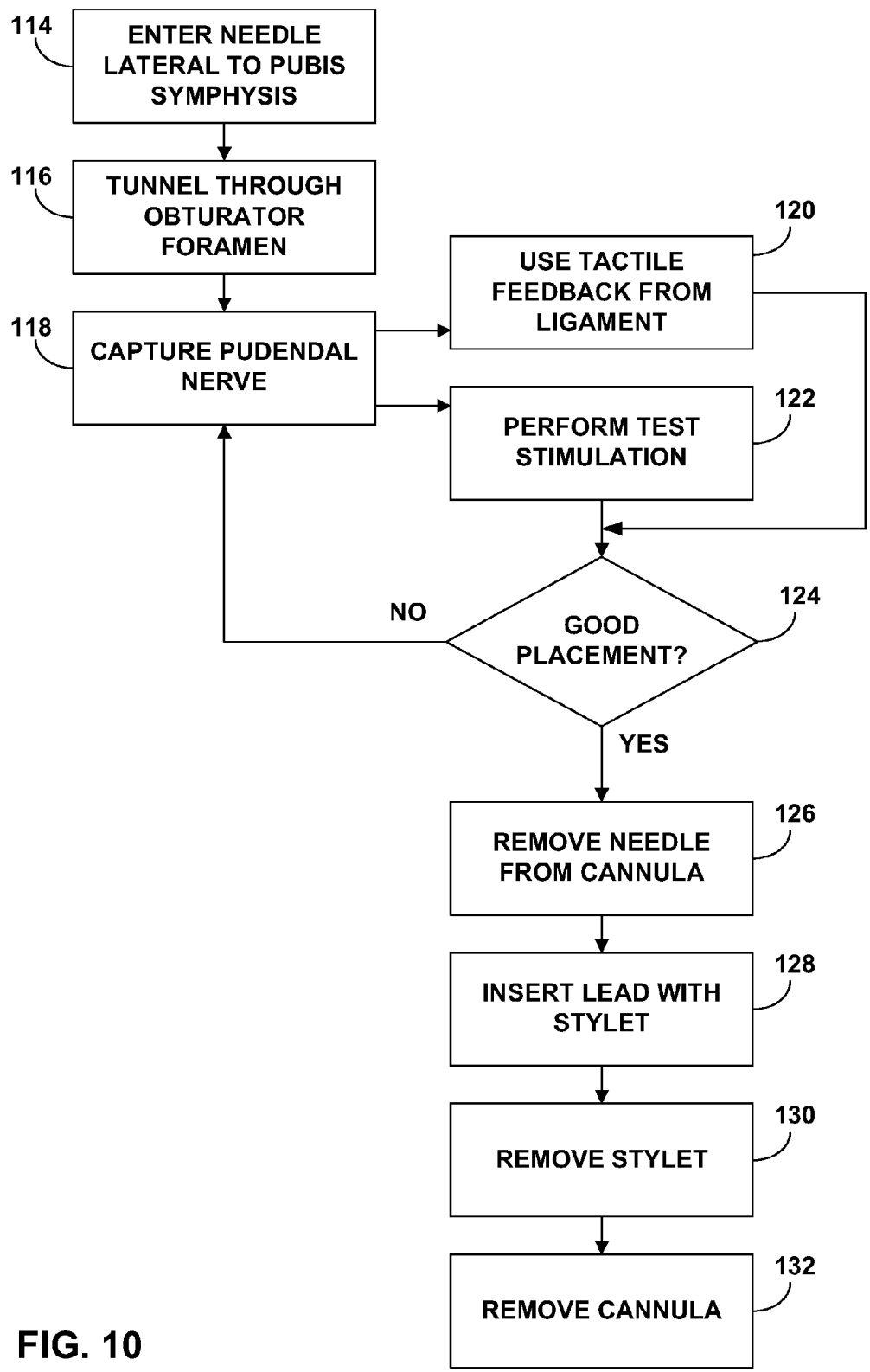
FIG. 10 is a flow chart illustrating a technique for implanting an electrical lead adjacent to a pudendal nerve.

FIG. 10 is a flow chart illustrating a technique for implanting an electrical lead adjacent to a pudendal nerve. The transobturator technique, or procedure, is described to provide a physician with a simple, effective, and repeatable method for accessing the pudendal nerve deep in pelvis 10 of a patient. Using implant tool 24 (implant tool 88 may also be used), in the example case of a female patient, a physician places needle 30 on skin of the pubic area between a vagina and interior thigh of the adjacent leg. Once the physician enters the vagina (or the rectum) with one or more fingers to palpate the ischial tuberosity 18 or ischial spine 12 trans-vaginally (or trans-rectally), the physician pierces the skin and inserts needle 30 lateral to the pubic symphysis of pelvis 10 toward obturator foramen 20 (114). Needle 30 is then tunneled through obturator foramen 20 by using a forward and up motion following the curve of needle 30 (116).

The goal is to capture pudendal nerve 40 by placing the tip of needle 30 adjacent to the pudendal nerve (118). A physician may use one or both of the following techniques to correctly capture pudendal nerve 40. The physician may use tactile feedback from needle 30 striking ligaments surrounding pudendal nerve 40 (120). For example, needle 30 may be retracted slightly if the needle contacts the sacrotuberous ligament posterior to pudendal nerve 40. In addition, the sacrospinous ligament may be used to locate an anterior edge of pudendal nerve 40 position. In addition to or alternatively, the physician may perform test stimulation to correctly position and capture pudendal nerve 40 (122). As described above, a separate test stimulation device or implant tool 88 may be used to deliver test pulses to pudendal nerve 40. The physician may observe muscle contractions or a CMAP of the sphincter to identify the location of needle 30 or needle 94 where stimulation is most effective. If the placement of needle 30 is not successful (124), the physician may attempt to capture pudendal nerve 40 once more (118). If the placement of needle 30 is successful, the physician may continue to implant the lead.

Once the placement of needle 30 is correct, the physician removes needle 30 from cannula 64 (126). Lead 46 (or any other lead described herein) is inserted into cannula 64 with a stylet to aid in navigating curves of the cannula (128). Once lead 46 is correctly placed adjacent pudendal nerve 40, the physician removes the stylet from lead 46 (130). The physician then removes cannula 64 from lead 46 to finish the implantation of the lead adjacent to pudendal nerve 40 (132).

In some embodiments, implant tool 52 may be used instead of implant tools 24 or 88. The procedure of FIG. 10 remains similar, with an alternative method in inserting needle 58. Implant tool 52 requires a twisting motion to tunnel helical needle 58 through obturator foramen 20 and reach pudendal nerve 40. In either case, the associated implant tool may aid in lead implantation at the pudendal nerve.

In other embodiments, the transobturator procedure of FIG. 10 may be similar when implanting a lead near a different nerve of the pelvic floor. For example, the procedure may be substantially similar when accessing the nerve of the clitoris. However, reaching the nerve of the clitoris may require a slightly different shaped needle 30 to appropriately position a lead adjacent to the nerve.

Figure 11:
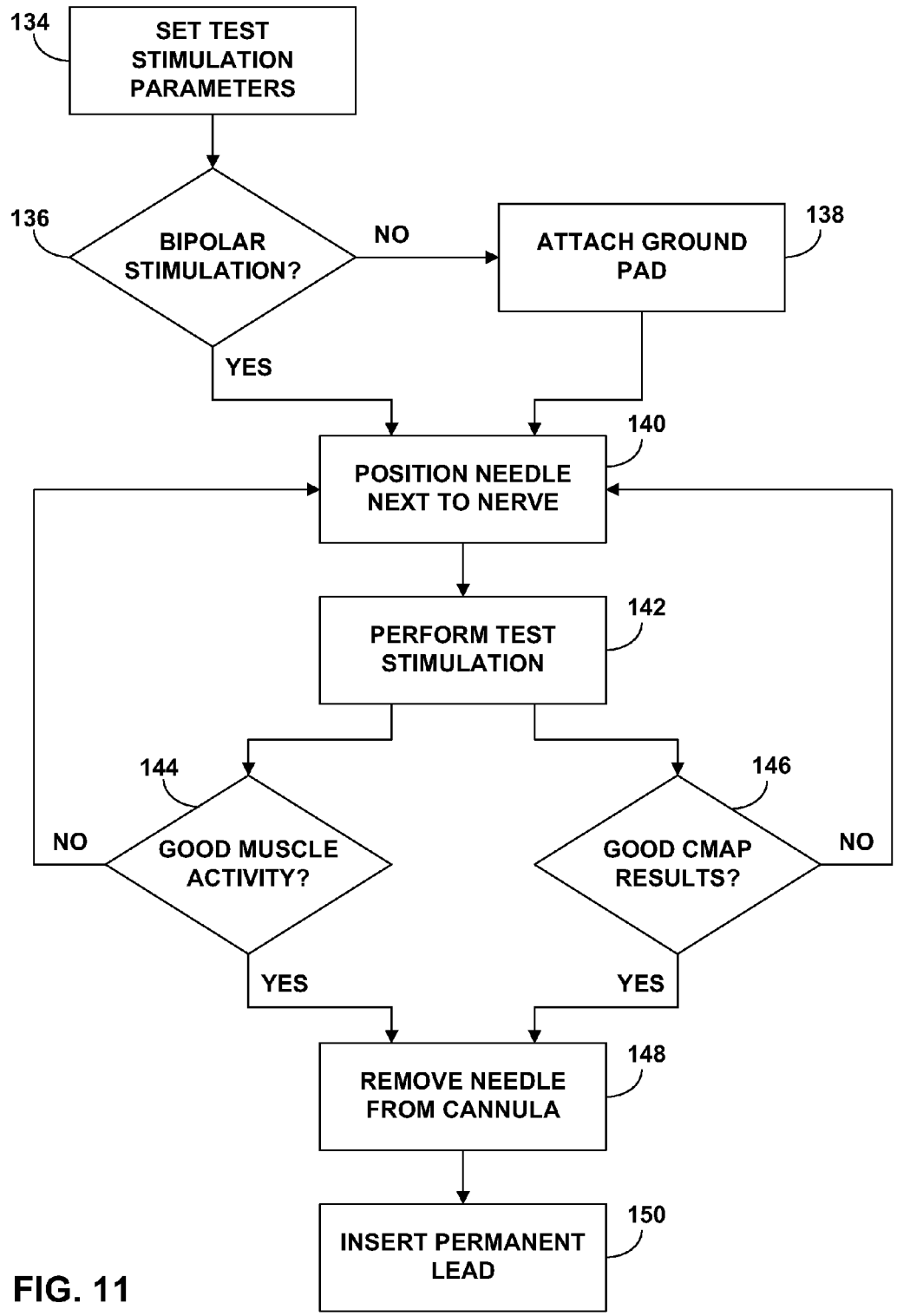
FIG. 11 is a flow chart illustrating a technique for performing test stimulation for determining the correct placement of an electrical lead.

FIG. 11 is a flow chart illustrating a technique for performing test stimulation for determining the correct placement of an electrical lead. Test stimulation may be completed with a test stimulation device coupled to implant tool 24 or with implant tool 88. Both test stimulation devices may be similarly operated. For purposes of illustration, implant tool 88 will be described.

Either before the transobturator procedure is performed or once needle 94 is located adjacent to pudendal nerve 40, the physician sets test stimulation parameters (134). Example parameters that may be set include current amplitude, voltage amplitude, pulse width, pulse frequency, or other parameters associated with stimulation of pudendal nerve 40. If implant tool 88 is configured for bipolar stimulation (136), the physician proceeds to position needle 94 adjacent pudendal nerve 40. If implant tool 88 is not configured for bipolar stimulation, such as unipolar stimulation, the physician must attach ground pad 98 to the patient and to implant tool 88 (138).

The physician positions needle 94 to a preferred location adjacent pudendal nerve 40 (140) and performs the test stimulation (142). The physician may look for good muscle activity associated with appropriate pudendal nerve 40 capture (144). If there is not good capture, the physician may reposition needle 94 (140). Alternatively, the physician may look for appropriate CMAP results from the test stimulation (146). If the CMAP results are not ideal, the physician may reposition needle 94 (140). In some embodiments, the physician may observe both muscle activity and CMAP results before accepting needle 94 location.

If the physician observes good muscle activity or good CMAP results, the physician may remove needle 94 from cannula 64 (148). Once needle 94 is removed, the physician may insert a lead and stylet into cannula 64 to finalize the implantation of the lead adjacent to pudendal nerve 40.

In some embodiments, the method of providing test stimulation with implant tool 88 may be used to provide test stimulation to other nerves. For example, implant tool 88 may be used to provide test stimulation to the nerve of the clitoris or other pelvic floor nerve.

Figure 12:
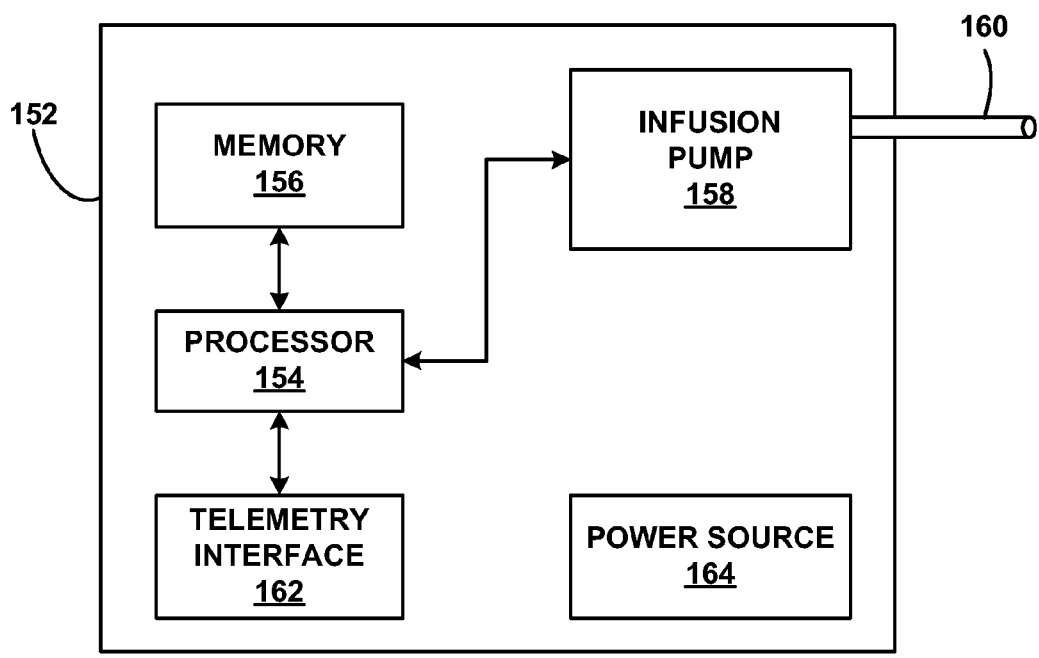
FIG. 12 is a functional block diagram illustrating various components of an implantable drug delivery device for providing neurostimulation.

FIG. 12 is a functional block diagram illustrating various components of implantable drug delivery device 152 for providing neurostimulation. As shown in FIG. 12, delivery device 152 includes processor 154, memory 156, infusion pump 158, telemetry interface 162, and power source 164. Delivery device 152 is implanted within patient 12 or located externally on patient 12. Catheter 160 is coupled to infusion pump 158 and implanted adjacent to a pelvic floor nerve, such as pudendal nerve 40. Catheter 160 may be implanted within patient 12 using implant tool 24, and the transobturator technique described herein. For example, catheter 160 may be introduced through the lumen of a needle or cannula deployed by the transobturator approach described herein. In some cases, cannula 64 may also be used to implant catheter 160 in the appropriate position. Accordingly, the lumen of cannula 64 or needle 30 may be sized to accommodate a catheter 160. Catheter 160 may be tunneled within patient 12 to an implanted device 152 or tunneled transcutaneously to an external delivery device 152.

Processor 154 controls the amount of drug dispensed by infusion pump 158 to patient 12. Processor 154 may use instructions stored within memory 156 to determine the time, amount, and frequency of drug delivery through catheter 160. Memory 156 may also store data related to the dispensing of drugs by infusion pump 158. Infusion pump 158 may continuously or periodically pump a liquid drug to patient 12. Telemetry interface 162 may communicate with an external program (not shown) to download new delivery instructions or upload delivery data. Power source 164 may include a rechargeable battery or induction coil produce power necessary for delivery device 152 operation.

Figure 13:
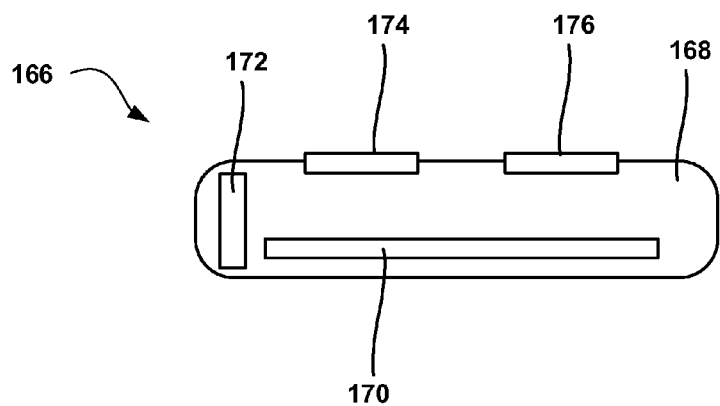
FIG. 13 is a schematic diagram illustrating an exemplary leadless stimulation module for stimulation of a nerve.

FIG. 13 is a schematic diagram illustrating an exemplary leadless electrical stimulation module 166 for electrical stimulation of a nerve. Stimulation module 166 includes implantable housing 168, circuit board 170, power supply 172, electrode 174, and electrode 176. Simulation module 166 may be implanted within patient 12, adjacent to a pelvic floor nerve, such as the pudendal nerve. Stimulation module 166 contains all necessary components to provide complete stimulation therapy without any lead or other wire connected to the module. Stimulation module 166 may be implanted using devices and techniques as described in this disclosure, including transobturator introduction techniques.

Housing 168 is biocompatible and protects the components of stimulation module 166 from corrosive biological fluids and tissues. Housing 168 may contain fixation mechanisms similar to lead 46 to secure stimulation module 166 near a desired nerve location. Circuit board 170 includes components such as a processor, memory, telemetry circuitry, or other electronics necessary for performing electrical stimulation. Power source 172 includes a battery or rechargeable battery to power the electrical circuitry of stimulation module 166. Power source 172 may also generate power through a trickle charger utilizing patient motion or induction with an external device. Electrodes 174 and 176 are attached to housing 168 and may be either a cathode or anode to provide electrical stimulation. In some embodiments, stimulation module 166 may include more than two electrodes. Alternatively, electrodes 174 or 176 may be tethered to housing 168 with a lead. In some embodiments, multiple leadless stimulation modules 166 may be implanted within the pelvic floor using devices and techniques as described in this disclosure.

Figure 14:
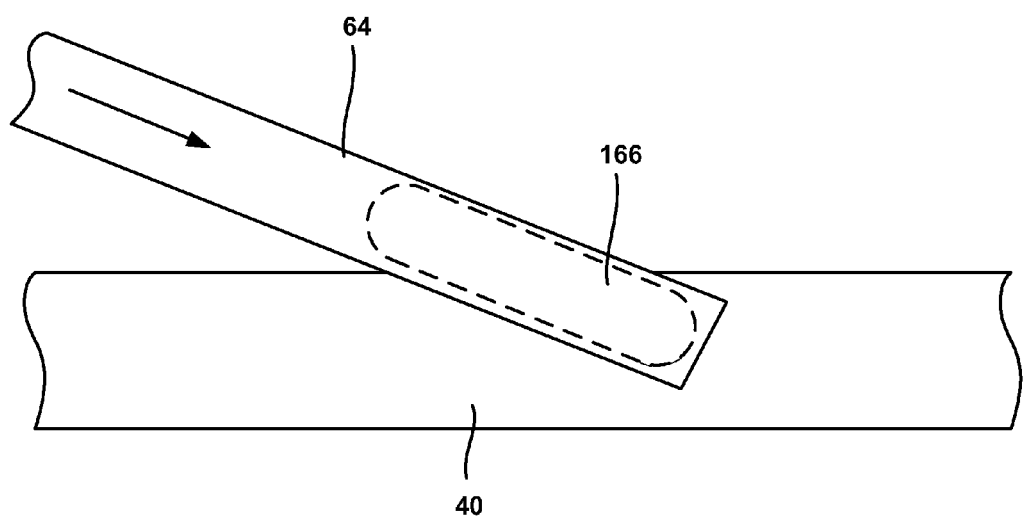
FIG. 14 is a schematic diagram illustrating implantation of a leadless stimulation module through a cannula.

FIG. 14 is a schematic diagram illustrating implantation of leadless stimulation module 166 through cannula 64. The inner lumen of cannula 64 may be sized to accommodate placement of module 166 through the inner lumen. Stimulation module 166 may be small enough to slide through the lumen of cannula 64 and implanted adjacent to pudendal nerve 40. Alternatively, stimulation module 166 may be implanted in tissue adjacent any pelvic floor nerve to provide stimulation therapy.

In other embodiments, stimulation module 166 may be implanted through needle 30 without cannula 64. In some cases, a guide wire or stylet may be used to aid in placing stimulation module 166 in an appropriate location. In addition, more than one stimulation module 166 may be placed adjacent to a nerve for effective stimulation therapy.

Various embodiments of the disclosure may include processors that are realized by microprocessors, Application-Specific Integrated Circuits (ASIC), Field-Programmable Gate Arrays (FPGA), or other equivalent integrated or discrete logic circuitry. The processor may also utilize several different types of data storage media to store computer-readable instructions for device operation. These memory and storage media types may include any form of computer-readable media such as magnetic or optical tape or disks, solid state volatile or non-volatile memory, including random access memory (RAM), read only memory (ROM), electronically programmable memory (EPROM or EEPROM), or flash memory.

Many embodiments of the disclosure have been described. Various modifications may be made without departing from the scope of the claims. These and other embodiments are within the scope of the following claims.

The invention claimed is:

1. A method comprising:
   introducing a tool through skin of a pubic area between a vagina and an adjacent leg of a patient;
   positioning at least a portion of the tool through an opening in a pelvis to a target nerve site within the patient; and
   implanting a medical device at the target nerve site through a path that terminates within the patient created by the tool.

2. The method of claim 1, wherein the opening in the pelvis comprises an obturator foramen.

3. The method of claim 1, further comprising inserting the tool through tissue lateral to a pubic symphysis of a pelvis of the patient.

4. The method of claim 1, wherein the implantable medical device includes a lead.

5. The method of claim 1, wherein the implantable medical device includes a leadless stimulation module.

6. The method of claim 1, wherein the implantable medical device includes a drug delivery catheter.

7. The method of claim 1, further comprising placing a distal tip of the tool adjacent to a pudendal nerve or a branch of the pudendal nerve.

8. The method of claim 7, wherein placing a distal tip of the tool includes slightly retracting a needle of the tool once the needle contacts a sacro-tuborosity ligament beyond the pudendal nerve.

9. The method of claim 1, further comprising delivering electrical stimulation via the tool to verify placement of a distal end of the tool adjacent the nerve.

10. A method comprising:
   introducing a tool into a patient lateral to a pubic symphysis of a pelvis of the patient;
   creating a path through an opening in the pelvis with the tool and positioning at least a portion of the tool at a target nerve site within the patient, wherein the opening in the pelvis is an obturator foramen, and wherein the path terminates within the patient; and
   implanting a medical device at the target nerve site through the path.

11. The method of claim 10, wherein the implantable medical device includes a lead.

12. The method of claim 10, wherein the implantable medical device includes a leadless stimulation module.

13. The method of claim 10, wherein the implantable medical device includes a drug delivery catheter.

14. The method of claim 10, wherein the target nerve site comprises a tissue site proximate to at least one of a pudendal nerve or a branch of the pudendal nerve.

15. The method of claim 14, further comprising placing a distal tip of the tool adjacent to the pudendal nerve or the branch of the pudendal nerve.

16. The method of claim 15, wherein placing a distal tip of the tool includes slightly retracting a needle of the tool once the needle contacts a sacro-tuborosity ligament beyond the pudendal nerve.

17. The method of claim 10, further comprising delivering electrical stimulation via the tool to verify placement of a distal end of the tool adjacent the nerve.

* * * * *